US005710046A

United States Patent [19]
Rutledge et al.

[11] Patent Number: 5,710,046
[45] Date of Patent: Jan. 20, 1998

[54] TAGGING HYDROCARBONS FOR SUBSEQUENT IDENTIFICATION

[75] Inventors: Michael J. Rutledge; Robert T. Roginski, both of Naperville; George H. Vickers, Aurora, all of Ill.

[73] Assignee: Amoco Corporation, Chicago, Ill.

[21] Appl. No.: 334,274

[22] Filed: Nov. 4, 1994

[51] Int. Cl.$^6$ .................................................. G01N 21/64
[52] U.S. Cl. ................................ 436/56; 436/27; 436/29; 436/172
[58] Field of Search ........................... 436/27, 29, 56, 436/172

[56] References Cited

U.S. PATENT DOCUMENTS

| | | |
|---|---|---|
| 3,733,178 | 5/1973 | Eriksen . |
| 3,806,727 | 4/1974 | Leonard et al. ............... 250/301 |
| 3,964,294 | 6/1976 | Shair et al. . |
| 4,009,008 | 2/1977 | Orelup . |
| 4,141,692 | 2/1979 | Keller . |
| 4,146,604 | 3/1979 | Kleinerman ..................... 424/3 |
| 4,278,444 | 7/1981 | Beyer et al. . |
| 4,301,372 | 11/1981 | Giering et al. . |
| 4,398,505 | 8/1983 | Cahill ............................ 123/1 A |
| 4,435,301 | 3/1984 | Brannen et al. . |
| 4,606,859 | 8/1986 | Duggan et al. ................ 540/122 |
| 4,666,672 | 5/1987 | Miller et al. .................... 422/68 |
| 4,755,469 | 7/1988 | Showalter et al. ............. 436/27 |
| 4,783,314 | 11/1988 | Hoots et al. .................... 422/3 |
| 4,904,567 | 2/1990 | Maeda et al. . |
| 4,978,625 | 12/1990 | Wagner et al. ................. 436/518 |
| 5,034,613 | 7/1991 | Denk et al. ..................... 250/458.1 |
| 5,093,147 | 3/1992 | Andrus et al. .................. 427/7 |
| 5,230,781 | 7/1993 | Middendorf et al. . |
| 5,254,625 | 10/1993 | Weaver et al. ................. 525/165 |
| 5,279,967 | 1/1994 | Bode ............................... 436/56 |
| 5,292,855 | 3/1994 | Krutak et al. .................. 528/289 |
| 5,302,740 | 4/1994 | Krutak et al. .................. 558/401 |
| 5,331,140 | 7/1994 | Stephany ........................ 235/462 |
| 5,525,516 | 6/1996 | Krutak et al. .................. 436/56 |

FOREIGN PATENT DOCUMENTS

| | | |
|---|---|---|
| 0134518 | 7/1984 | European Pat. Off. . |
| 0361310 | 11/1931 | United Kingdom . |
| 9208676 | 5/1992 | WIPO . |
| 9309172 | 5/1993 | WIPO . |
| 9402570 | 2/1994 | WIPO . |
| 9404918 | 3/1994 | WIPO . |
| 9412874 | 6/1994 | WIPO . |

OTHER PUBLICATIONS

Report: "Oil Tagging System Study"; Research Division, Environmental and Applied Sciences Center (May 1970).
Report: "A Study of Oil Source Identification Techniques"; L. Melamed, Environmental and Transportation Technology Division Office of Research and Development (Sep. 1972).
Paper: "Triplet States of Copper and Metal–free Phthalocyanines"; James McVie, Roy S. Sinclair and T. George Truscott (Mar. 1978) Chemistry Department, Paisley College, Paisley, Scotland.
Article: "Naphthoquinone Colouring Matters. Part 2.—1, 4–Naphthoquinones with Electron–donating Groups in the Benzenoid Ring"; Kwong–Yung Chu and John Griffiths, *Journal of Chemical Research (S)* 1978, 180–181.

(List continued on next page.)

*Primary Examiner*—Jill Warden
*Assistant Examiner*—Sharidan Carrillo
*Attorney, Agent, or Firm*—Robert A. Yesukevich; Frank J. Sroka; Richard A. Kretchmer

[57] ABSTRACT

A method for tagging hydrocarbons and for detecting the presence of tagged hydrocarbons in a hydrocarbon mixture. The method can be utilized to tag gasoline, diesel fuel, heating oil, lubricating oil or crude petroleum. The hydrocarbon to be tagged is blended with a relatively small amount of a fluorescent dye. The presence of the tagged hydrocarbon is subsequently determined by exciting the dye to fluoresce at wavelengths in the higher portion of the visible spectral region or the lower portion of the near infrared spectral region.

10 Claims, 9 Drawing Sheets

OTHER PUBLICATIONS

Article: "Picosecond Laser Photophysics, Group 3A Phthalocyanines"; James H. Brannon and Douglas Magde, *Journal of the American Chemical Society* 102.1, Jan. 2, 1990.

Article: "Excited Singlet and Triplet State Electron–transfer Reactions of Aluminium(III) Sulphonated Phthalocyanine"; James R. Darwent, et al., *Journal Chemical Society*, Faraday Trans. 2, 1982, vol. 78, 347–357.

Article: "Photochemistry of Transition–Metal Phthalocyanines"; G. Ferraudi and S. Muralidharan, *Journal of Inorganic Chemistry*, 1983, vol. 22, 1369–1374.

ARticle: "Semiconductor Laser Fluorimetry in the Near–Infrared Region"; Totaro Imasaka, et al., *Analytical Chemistry*, 1984, vol. 58, 1077–1079.

Article: "A Silicon Phthalocyanine and a Silicon Naphthalocyanine: Synthesis, Electrochemistry, and Electrogenerated Chemiluminescence"; Bob L. Wheeler, et al., *Journal of the American Chemical Society*, 1984, vol. 106, 7404–7410.

Article: "Comparison of Calculated Detection Limits in Molecular Absorption, Molecular Luminescence, Raman, Molecular Ionization, and Photothermal Spectrometry"; J. D. Winefordner and M. Rutledge, *Applied Spectroscopy*, 1985, vol. 39, No. 3, 377–391.

Article: "Determination of Protein in Human Serum by High–Performance Liquid Chromatography with Semiconductor Laser Fluorometric Detection"; Kouji Sauda, et al., *Analytical Chemistry*, vol. 58, No. 13, Nov. 1986.

Article: "Estimation of Absolute Number Densities From Shapes of Atomic Fluorescence Curves of Growth"; B.W. Smith, M.J. Rutledge et al., *Applied Spectroscopy*, 1987, vol. 41, No. 4, 613–620.

Abstract: "An Overview of Advanced Spectroscopic Field Screening and In–Situ Monitoring Instrumentation and Methods"; D. Eastwood, et al., *Chemistry for the Protection of the Environment*, Eds. Pawlowski, et al., Plenum Press, New York, 1991.

Article: "The Structures and Vibrational Dynamics of Small Carbon Clusters"; James R. Heath and Richard J. Saykally, *On Clusters and Clustering: From Atoms to Fractals*, Ed. P.J. Reynolds, Elsevier Science, 1993, 7–21.

Article: "Infrared Laser Spectroscopy of Jet–Cooled Carbon Clusters Structure of Triplet $C_6$"; H.J. Hwang, et al., *Molecular Physics*, 1993, vol. 79, No. 4, 769–776.

Article: "Near–Infrared Absorbing Dyes"; Jurgen Fabian, et al., *Chemical Reviews*, 1992, vol. 92, No. 6, 1197–1126.

Article: "Steady–State and Picosecond Laser Fluorescence Studies of Nonradiative Pathways in Tricarbocyanine Dyes: Implications to the Design of Near–IR Fluorochromes with High Fluorescence Efficiencies"; Steven A. Soper and Quincy L. Mattingly, *Journal of American Chemical Society*, 1994, vol. 116, No. 9, 3744–3752.

Article: "Identification of Petroleum Oils by Fluorescence Spectroscopy"; U.Frank, *Proceedings of the 1975 Conference on Prevention and Control of Oil Pollution*, San Francisco, California, Mar. 25–27, 1975, pp. 87–91.

TAGGING HYDROCARBONS FOR SUBSEQUENT IDENTIFICATION

BACKGROUND OF THE INVENTION

1. Field of the Invention

The present invention relates to a method for tagging hydrocarbons which permits the presence of such hydrocarbons, especially as components of hydrocarbon mixtures, to be subsequently detected. The invention also relates to devices for detecting the tagged hydrocarbons and to fluorescent dyes appropriate for tagging hydrocarbons.

2. Description of the Prior Art

Hydrocarbon mixtures are, by their very nature, difficult to characterize and identify. Hydrocarbons are composed predominantly of carbon and hydrogen atoms, but can also contain relatively minor amounts of elements such as oxygen, nitrogen, phosphorous and sulfur. Aliphatic hydrocarbons consist of chains of carbon atoms that do not involve cyclic structures. Cyclic hydrocarbons are composed of atoms arranged in a ring or rings. Aromatic hydrocarbons are a sub-set of cyclic compounds having six membered rings which share hybrid carbon-carbon bonds. Other hydrocarbons are constituted by rings and chains, and may be aromatic to some extent.

Petroleum and associated natural gases are currently the major source of hydrocarbons. Petroleum is a complex mixture in which aliphatic, cyclic and aromatic hydrocarbons are present. Separation processes such as distillation and extraction separate crude petroleum into useful fractions, while conversion processes such as catalytic cracking create fractions not found in nature. For example, a gasoline fraction which can be recovered from petroleum encompasses a range of $C_5$–$C_{10}$ compounds having boiling points of about 40° to about 200° C. Other principal fractions which can be recovered from petroleum are kerosene which includes $C_8$–$C_{14}$ compounds and has a boiling point range of about 175° to about 325° C., gas oil which includes $C_{12}$–$C_{18}$ compounds and has a boiling point above 275° C., and lubricating oils.

Additionally, the characterization of many petroleum fractions is further complicated as the recovered fractions are blended with other fractions, chemically transformed or dosed with additives. Additives include octane enhancers, oxygenates, corrosion inhibitors and deposition inhibitors. Analytical procedures for detecting the presence of certain hydrocarbons in hydrocarbon mixtures are known. However, traditional analytical procedures are time-consuming and often provide only limited information about the mixtures.

The oil industry has recognized the need for a distinctive tagging agent or tracer which could be used to quickly and efficiently distinguish between seemingly identical mixtures of hydrocarbons, or, alternatively, to identify their manufacturing source or commercial destination. For example, a paper entitled "Identification of Petroleum Oils by Fluorescence Spectroscopy" by U. Frank was published in the Proceedings of the 1975 Conference on Prevention and Control of Oil Pollution, San Francisco, Calif., Mar. 25–27, 1975, pages 87–91. The Frank paper describes a method of passive tagging by fluorescence spectroscopy which involves excitation of petroleum oils at 15 wavelengths between 225 and 500 nanometers, at 20 nanometer intervals. The Frank paper states that the maximum emission intensities are plotted versus the excitation wavelengths to derive silhouette profiles used as fingerprints for passive tagging.

Passive tagging has been criticized, however, on the grounds that the naturally occurring compounds available for use as passive tags are not sufficiently identifiable and stabile. As alternatives, three methods of active tagging are recommended in a paper entitled "Oil Tagging Systems Study" published by the National Technical Information Society in May of 1970 under NTIS Accession No. PB-195 283. Halogenated polycyclic aromatics, organometallics, and coded microspheroids were reportedly examined and found to show promise as active tags for oils.

U.S. Pat. No. 4,755,469 issued to Showalter et al. describes a method for tagging an oil so that it may be subsequently identified. The Showalter et al. patent states that a rare earth metal salt of a fatty acid can be incorporated into the oil and, thereafter, an oil suspected to contain at least a portion of the tagged oil may be analyzed for the presence of the rare earth metal. However, conventional techniques which analyze for the presence of rare earth metals are typically expensive and time consuming.

A method for determining the presence of one or more liquid hydrocarbons in a liquid hydrocarbon mixture is described in U.S. Pat. No. 4,278,444 issued to Beyer. The method reportedly involves adding to the hydrocarbon to be detected a minor amount of an alkylated isodibenzanthrone which can subsequently be detected by means of fluorescence spectroscopy. The Beyer et al. patent recounts a procedure in which alkylated isodibenzanthrone is excited to fluorescence by visible light and emits fluorescent light in the visible spectrum. Such a procedure appears to be less satisfactory for use in hydrocarbons which naturally possess a significant degree of visible color or contain a visible artificial dye.

U.S. Pat. No. 5,279,967 issued to Bode describes a hydrocarbon liquid identification and tracing system based on fluorescence, chromatographic separation and the presence or absence of substituted naphthalimides. According to the Bode patent, one or more of a homologous series of substituted naphthalimide dyes, which absorb and fluoresce light in the visible spectrum, can be added to a hydrocarbon fluid in varying amounts as labels. The Bode et al. patent lists an excitation range for gasoline of 350–440 nanometers and an emission range for gasoline of 450–550 nanometers, and describes the substituted naphthalimides which reportedly emit at 550 nanometers as having acceptable excitation and emission spectra for use with gasoline.

Subsequently, the labeled hydrocarbon fluid is passed through a separation device, such as a chromatograph, to separate the labeling compounds from the hydrocarbon fluids and to detect the presence or absence of the labeling fluids according to their separation and fluorescent characteristics. The necessity of providing a chromatograph or other separation device seemingly disqualifies the system described in the Bode patent from consideration for applications requiring portability or a speedy determination.

U.S. Pat. No. 4,141,692 issued to Keller discusses a method of marking fuels with chlorohydrocarbon or chlorocarbon tracers. The tracers reportedly can be detected by gas chromatography using a pulsed electron capture detector. The method is said to be applicable to gasolines, diesel fuels, jet fuels, furnace oils, and kerosenes. Practitioners will appreciate, however, that the use of such chlorine containing tracers in fuel tends to increase the rate of metallic corrosion in associated engines or burners and also to increase the level of objectionable pollutants in combustion products.

The term dye refers to compositions of matter exhibiting absorption peaks at reproducible wavelengths. Fluorescent dyes are defined for the present purposes as compositions of matter exhibiting absorption peaks at reproducible wavelengths and, thereafter, emitting fluorescence radiation.

Known fluorescent dyes include, for example, polymethines. One such polymethine, 3,3'-diethyl-2,2'-(4,5', 4',5'-dibenzo) thiatricarbocyanine iodide (hereinafter, "DDTC"), is described in an article entitled "Semi-Conductor Laser Fluorimetry in the Near-Infrared Region" by Imasaka et al., Analytical Chemistry, 1984, 58, 1077–1079 (June 1984). The article states that DDTC exhibits strong absorption in the region of 786 nanometers and fluoresces at approximately 840 nanometers when dispersed in methanol or benzene. The article also states that DDTC was less soluble and completely non-fluorescent in water. A procedure in which a semi-conductor laser fluorimeter was utilized to demonstrate trace analysis of surfactants based on ion-pair extraction of DDTC is reported.

An infrared absorbing phthalocyanine compound having organic substituents linked to at least 5 of 8 specified peripheral carbon atom positions is described in U.S. Pat. No. 4,606,859 issued to Duggan et al. The phthalocyanine compounds are said to absorb in the range 750 to 1100 nanometers. The Duggan et al. patent states that the organic substituents may be aliphatic, alicyclic or aromatic. The Duggan et al. patent proposes the phthalocyanine compound for use in absorbing electromagnetic energy from an infrared source, as in use with infrared inks or welding goggles.

Hydrocarbon-soluble, metal-containing naphthalocyanine compounds are reported in European Patent Application 84108500.4 which lists Tsunehito as inventor. The Tsunehito application states that the naphthalocyanine compounds are soluble in organic solvents and exhibit strong absorption of near-infrared radiation in the range of 750 to 850 nanometers. The application lists absorption peak wavelengths and absorptivity co-efficients for several metal-containing naphthalocyanine compounds, but is silent on the subject of fluorescence. The described naphthalocyanine compounds have straight chain or branched chain alkyl groups, each of the alkyl groups having 5 to 12 carbon atoms.

Squarylium dyes, also called squaraines, are being marketed as near infrared photoreceptors for laser printers, according to an article entitled "Near-Infrared Absorbing Dyes," Chemical Review, 1992, No. 6, 1197–1226 (July 1992) by Fabian et al. The Fabian et al. article states that a symmetrical squarylium exhibits photoconductivity at 830 nanometers. However, the Fabian et al. article is silent on the subject of fluorescence for squarylium dyes.

Methods for tagging and for detecting and separating thermoplastic containers using near-infrared fluorescing compounds are proposed in International Application No. PCT/US92/08676 which lists Cushman et al. as inventors. The method for detecting and separating thermoplastic containers reportedly includes exposing a mixture of thermoplastic containers to near-infrared radiation having wavelengths of about 670 to about 2500 nanometers, detecting emitted fluorescent light, and separating the fluorescing containers from non-fluorescing containers by mechanical means. FIG. 1 of the Cushman et al. application depicts an apparatus for identifying thermoplastic polymers containing a near-infrared marker.

The Cushman et al. application reports that phthalocyanines, naphthalocyanines, and squaraines are useful as markers. Significantly, the Cushman et al. application states that the near-infrared fluorescing compounds must be thermally stabile and suitable for admixing or copolymerizing with condensation polymers. Moreover, the Cushman et al. application notes that the markers may be employed as copolymers to produce marked thermoplastic compositions in which the marker is not readily separated.

A portable fluorescence instrument including ultraviolet excitation optics and fluorescence spectral optics is described in U.S. Pat. No. 4,301,372 issued to Giering et al. The fluorescence instrument reportedly includes an ultraviolet radiation source, such as a low-pressure mercury lamp. The Giering et al. patent states that the ultraviolet radiation is absorbed by most aromatic hydrocarbons which fluoresce. A fluorescence spectrum of the sample under examination is reportedly recorded by the instrument.

Despite the significant achievements of previous practitioners, a need still exists for an improved system of marking hydrocarbons and determining their presence. Preferably, the improved system includes a marker which is invisible to the naked eye, yet detectable by a relatively quick and simple test procedure. Preferably, the test procedure requires minimal instrumentation and creates no waste products for disposal. Desirably, the improved system permits detection of the marked hydrocarbon at comparatively low concentrations in mixtures with other hydrocarbons.

The limitations of traditional marking methods are perhaps best illustrated by reference to a problem currently facing gasoline regulators, producers, transporters and retailers. Reformulated gasoline conforms to stringent standards intended to reduce air pollution associated with automobiles. To achieve the benefit of reduced air pollution, the sale of conventional gasoline may soon be prohibited in certain areas of the United States. Enforcing such a prohibition is problematical because the visual appearance of reformulated gasoline and conventional gasoline is quite similar. Therefore, the Environmental Protection Agency of the United States Government (hereinafter, "EPA") is currently evaluating gasoline markers to assist in distinguishing reformulated gasoline from conventional gasoline.

The EPA's published criteria for conventional gasoline markers are cost-effectiveness, wide availability, stability, minimal environmental side effects and enforceability. Factors which affect the stability of the marker include the extent to which the marker forms deposits on gasoline-powered engines, the extent to which the marker interacts with gasoline additives, and the solubility of the marker in water (which is sometimes present in gasoline storage tanks). One factor affecting environmental side effects is whether detection of the marker creates waste products for disposal. Similarly, gasoline markers which contain metals, sulfur or chlorine tend to produce combustion products having adverse environmental side effects.

None of the previously known gasoline marker systems satisfy all of the EPA criteria. Moreover, of five conventional gasoline markers which the EPA is currently evaluating for use in distinguishing reformulated gasoline from conventional gasoline, one must be administered at dosages which form solid deposits in gasoline-powered engines. Another marker being evaluated reacts with detergent additives commonly employed in gasoline. The other three markers being evaluated are detected by means of chemical detection kits which produce waste materials necessitating disposal. These shortcomings are not oversights but, rather, limitations imposed by current marker technology. In light of these shortcomings, it is believed that an improved system for marking gasolines would be welcomed by government, industry, and consumers.

SUMMARY OF THE INVENTION

The present invention is a system for tagging hydrocarbons by means of fluorescent dyes and for determining the presence of the tagged hydrocarbons by exciting the dyes to fluoresce at wavelengths of about 600 to about 2,500 nanometers. The system provides a desirably low detection threshold. Additionally, the excitation and the fluorescence take place in a spectral region which is remarkably free from background interference. In other aspects, the invention is a method for tagging and identifying hydrocarbons, an apparatus for identifying hydrocarbons, and a fluorescent dye for tagging hydrocarbons.

In one aspect, the invention is a method for identifying a sample containing a tagged gasoline. The dye is capable of absorbing radiation in a predictable absorption band to facilitate a transition from a relatively lower energy state to an excited state. The method comprises irradiating the sample with radiation in an excitation band which has wavelengths in common with the absorption band. Upon returning to the lower energy state, the sample emits fluorescence radiation in a predictable fluorescent band. The fluorescence radiation is detected and a detection signal is generated.

In another aspect, the invention is a method for identifying a gasoline sample containing a fluorescent dye. The method includes generating radiation having wavelengths of about 600 to about 2,500 nanometers which describes an excitation path from an excitation source to a target chamber. The generated radiation is utilized to irradiate a sample containing an appropriate fluorescent dye in the target chamber. As a result, the sample emits fluorescence radiation in a fluorescent band which is passed to a detector. Detection of a predetermined amount of radiation triggers a detection signal.

In still another aspect, the invention is a method for detecting the presence of a tagged gasoline dispersed in a liquid. Radiation in an excitation band describing an excitation path is generated, as described above. A submersible head is immersed in the liquid, which contains an appropriate fluorescent dye. Located opposite an excitation path terminus is a target volume, defined by the head, containing a portion of the liquid. The target volume is irradiated by radiation in the excitation band at an intensity sufficient to cause the dye to emit fluorescence radiation which describes a fluorescence path. A detector situated opposite a fluorescence path terminus detects the fluorescence radiation and produces a detection signal.

In an additional aspect, the invention is a method for tagging hydrocarbons which comprises blending a fluorescent dye at a concentration of about 0.01 to about 1000 parts per billion. The dye is preferably substantially hydrocarbon-soluble, yet essentially water-insoluble. Suitable fluorescent dyes can be selected from the group consisting of naphthalocyanine dye, phthalocyanine dye, cyanine dye, methine dye, croconium dye and squarylium dye. Preferably the fluorescent dyes absorb and fluoresce at wavelengths in the range of about 600 to about 2500 nanometers.

In yet another aspect, the invention is an apparatus for detecting the presence of a fluorescent dye in a hydrocarbon sample. The apparatus comprises an excitation source adapted for generating radiation in an excitation band including wavelengths of about 600 to about 2500 nanometers. The generated radiation describes an excitation path extending to a sample receiver which defines a target chamber opposite a terminus of the excitation path. The target chamber is adapted for exposing a hydrocarbon sample in the target chamber to radiation in the excitation band. The target chamber is also adapted for receiving radiation from the sample. As a result of exposure to radiation in the excitation band, the fluorescent dye emits fluorescence radiation which describes a fluorescence path. A detector is located opposite an excitation path terminus to detect the fluorescence radiation, whereupon a detection signal is generated.

In another aspect still, the invention is an apparatus for detecting the presence of a tagged hydrocarbon dispersed in a liquid. The apparatus comprises a generator assembly for generating radiation in an excitation band, as described above. A submersible head defines a target volume opposite an excitation path terminus. The target volume communicates with a liquid containing tagged hydrocarbon so that the liquid enters the target volume when the head is immersed. Radiation from the generator assembly excites a fluorescent dye, as described above, contained in the liquid, so that the liquid emits fluorescence radiation along a fluorescence path. A detector is situated opposite a terminus of the fluorescence path to sense the radiation and give rise to a detection signal.

Other aspects of the invention include a fluorescent dye suitable for tagging gasolines.

DETAILED DESCRIPTION OF PREFERRED ASPECTS OF THE INVENTION

Figure 1:
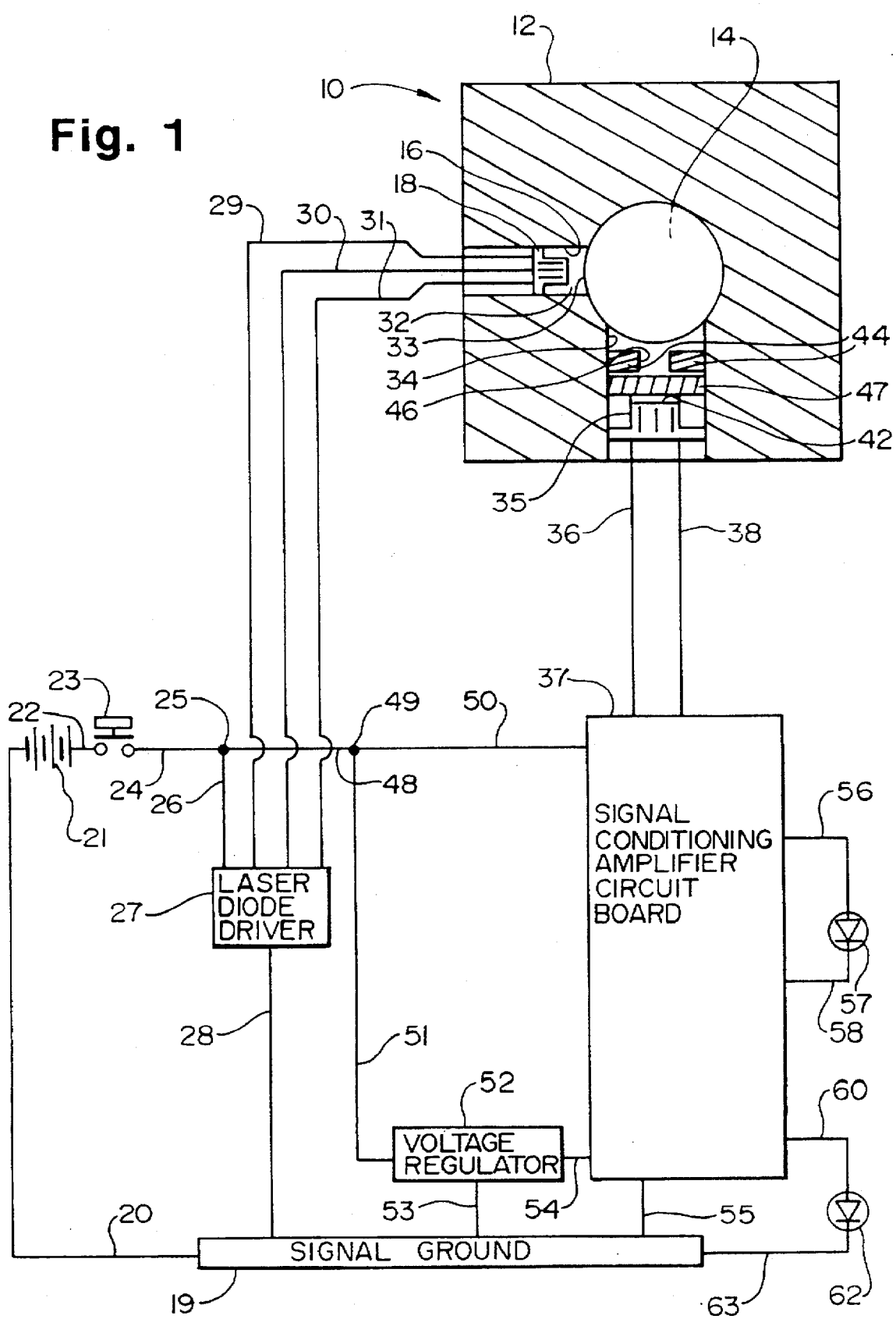
FIG. 1 is a schematic diagram of an apparatus for detecting the presence of a fluorescent dye in a hydrocarbon sample, with a sample receiver which houses an excitation source and a detector shown in cross-sectional plan view.

When stimulated to an excited state by, for example, absorbing radiation, most gasolines fluoresce in the ultraviolet and the visible regions. However, naturally occurring gasoline fluorescence signals are considerably weaker towards the high end of the visible region and still weaker in the near infrared region, at wavelengths of about 600 to about 2,500 nanometers. The region of about 630 nanometers or more, and especially of about 700 nanometers or more, provides a quiet zone where there is relatively little fluorescence by gasolines. This quiet zone persists to some extent even when the gasoline is admixed with other hydrocarbons.

Moreover, gasolines generally absorb electromagnetic radiation in the ultraviolet region, at wavelengths of about 100 to about 330 nanometers. The primary absorbers of such ultraviolet radiation are aromatic molecules undergoing electronic transitions. To a lesser degree, gasolines also absorb radiation in the visible range, at wavelengths of about 330 to about 650 nanometers. Absorption in the visible range is commonly due to color bodies which are naturally present in gasoline. Some of the color bodies have been determined to be olefinic hydrocarbon molecules or polynuclear aromatic hydrocarbon molecules.

Some gasoline manufacturers presently employ artificial visible dyes to color gasolines. The presence of these dyes can identify various grades of gasoline, distinguish the products of a particular manufacturer in the market place, or mark the passage of interface cuts in transportation pipelines. Yellow, red, blue and purple dyes have traditionally been employed. Dyes having primary colors are currently utilized to mark grades of diesel fuel and identify sulfur levels in fuels.

The visible dyes used for these marking purposes typically absorb radiation in the 400 to 700 nanometer range. Often, the visible dyes simultaneously absorb a significant amount of ultraviolet radiation. The presence of these visible dyes tends to interfere with the detection of other dyes which absorb or fluoresce in the visible and ultraviolet regions.

Gasolines naturally absorb electromagnetic radiation in the near infrared region to some extent. For example, carbon to hydrogen bonds, which are prevalent in gasolines, absorb radiation by a mechanism associated with vibrational bond stretching at a primary absorption wavelength in the range of about 3,000 to about 3,500 nanometers. The carbon to hydrogen bonds also absorb radiation at wavelengths known as harmonic overtones, which are essentially integer factors of the primary absorption wavelength. However, partly because each of the succeeding harmonic overtones generally gives rise to relatively weaker absorbance peaks, the region of the infrared spectrum located below about 850 nanometers is remarkably absorption free. Therefore, the region of about 600 to about 2,500 nanometers, preferably about 630 to about 850 nanometers, and most preferably about 700 to about 800 nanometers, provides an excellent region for the practice of the present invention.

In one aspect, the invention is a method for identifying a sample containing a tagged gasoline. The gasoline is tagged in the sense that it contains a fluorescent dye which is capable of absorbing and fluorescing electromagnetic radiation at predetermined wavelengths in the infrared region of the spectrum. The fluorescent dye is preferably present in the tagged gasoline at a concentration of about 0.01 to about 1,000 ppb, more preferably about 0.1 to about 500 ppb, and most preferably at about 1 to about 100 ppb.

Absorbance (A) is the base ten logarithm of the ratio of incident power ($I_O$) to transmitted power (I) associated with the passage of electromagnetic radiation through a medium, according to the formula $A=\log_{10} I_O/I$. The absorbance of a particular fluorescent dye in a given mixture can be expressed as a function of incident radiation wavelength. Absorption peaks are herein defined as the maxima of such absorbance functions. Incident radiation having wavelengths at or near an absorption peak, so as to be strongly absorbed by the fluorescent dye, is said to include radiation in an absorption band. It is preferred that the fluorescent dyes employed in the present invention have an absorption band of about 600 to about 2,500 nanometers, with about 630 to about 830 nanometers being more preferred, and about 700 to about 800 nanometers being especially preferred. For the present purposes, strongly absorbing is understood to mean having a molar absorptivity of at least about 100,000 $M^{-1}cm^{-1}$.

Preferably the radiation in the excitation band includes wavelengths of about 600 to about 2,500 nanometers, more preferably about 630 to about 830 nanometers, and most preferably about 700 to about 800 nanometers, at an intensity appropriate and with sufficient overlap with the absorption band to stimulate the fluorescent dye from a lower energy level to an excited state. Thereafter, the fluorescent dye spontaneously returns to the lower energy level. The transition to the lower energy level is accompanied by an emission of fluorescence radiation.

The fluorescent dye emits the fluorescence radiation isotropically in predictable fluorescent bands. The fluorescent bands include wavelengths which are about equal to or greater than the wavelengths of the stimulating absorption bands. Preferably the fluorescent bands include wavelengths of about 600 to about 2,500 nanometers, more preferably about 650 to about 850 nanometers, and most preferably about 700 to about 830 nanometers.

The irradiating can be accomplished by means of any electromagnetic radiation source having an appropriate wavelength range and suitable intensity. Sources which can be focused or directed to produce, for example, a beam are preferred. Similarly, sources which inherently produce radiation in a relatively narrow wavelength band are especially preferred. For example, the source may be a laser.

A laser is herein defined, for the present purposes, as a device which has the ability to produce monochromatic, coherent light through the stimulated emission of photons from atoms, molecules, or ions of an active medium which has typically been excited from a ground state to a higher energy level by an input of energy. Such a device typically contains an optical cavity or resonator which is defined by highly reflecting surfaces forming a closed roundtrip path for light, and the active medium is contained within the optical cavity.

Laser diodes are especially preferred for use as the excitation source. As compared to other types of laser, laser diodes are relatively portable, durable and inexpensive. Such laser diodes are commonly attached to thermally conductive heat sinks and are packaged in metal housings. A dedicated photodiode is often included within the metal housing to provide a feedback signal which aids on adjusting power input to the laser diode. Laser diodes are available which, as a function of composition, produce output radiation having a wavelength over the range of about 600 to about 1,600 nanometers.

For example, the wavelength of the output radiation from a gallium-indium-phosphorus-based device (GaInP) can be varied from about 600 to about 700 nanometers by variation of the device composition. Similarly, the wavelength of the output radiation from a gallium-aluminum-arsenic-based device (GaAlAs) can be varied from about 750 to about 900 nanometers by variation of the device composition. Indium-gallium-arsenic-phosphorus-based devices (InGaAsP) can be used to provide radiation in the wavelength range from about 1,000 to about 1,600 nanometers.

Additionally, a laser diode or laser diode array typically can be tuned over a wavelength range of about ten nanometers by adjusting and controlling its operating temperature. The range of available wavelengths can be extended by such well-known techniques as sum-frequency generation. An example of an especially preferred excitation source is the GaAlAs diode laser.

The method further comprises detecting the presence of radiation in the fluorescent band emanating from the sample. Preferably, the method employs a detector including one or more photodiodes arranged to receive radiation from a direction other than that in which radiation emanates from the excitation source. More preferably, the detector faces in a direction at right angles to the direction of the excitation source. A shield plate constructed of material substantially opaque to radiation in the excitation band but defining a relatively small aperture to pass radiation travelling in a certain direction can be positioned adjacent the detector to narrow the field monitored by the detector. Similarly, a wavelength selective filter can be situated adjacent the detector to at least partially block radiation which is not in the fluorescent band. The wavelength selective filter is especially useful for protecting the detector from scattered excitation radiation.

In another aspect, the invention is a method for identifying a gasoline containing a fluorescent dye. In the method, radiation is generated in an excitation band, described above, by an excitation source. Preferred methods of generating the radiation utilize laser diodes, as described above. The radiation in the excitation bands, if not initially unidirectional, is focused or reflected to describe an excitation path emanating from the excitation source. The excitation path may be unfettered, as in the case of a radiation beam traveling through a vacuum. Alternatively, the excitation path may be guided and adjusted, as by mirrors or by internal reflecting surfaces of fiber optic cables. The excitation path extends to a target chamber.

In the target chamber, the gasoline sample is irradiated by the excitation radiation. The sample contains a fluorescent dye appropriate for emitting radiation in the fluorescent band, as described above. The fluorescent dye is appropriate for emitting radiation in the fluorescent band as a result of exposure to radiation in the excitation band.

Preferred fluorescent dyes are selected from the group consisting of polymethine dyes, cyanine dyes, phthalocyanine dyes, naphthalocyanine dyes, croconium dyes and squarylium dyes. The fluorescent dyes absorb and fluoresce radiation in the wavelength ranges specified above. Additionally, preferred fluorescent dyes are soluble in hydrocarbons. Especially preferred fluorescent dyes are soluble up to at least about one percent by weight in gasoline. Relatively soluble fluorescent dyes permit the preparation of intermediate concentration mixtures which can aid in blending and distributing the fluorescent dye throughout a final mixture.

Moreover, the preferred fluorescent dye is essentially insoluble in water. A separate water phase is often found in hydrocarbon storage tanks, for example, from condensation. A dye which is soluble in water can be leached out of the tagged hydrocarbon into the water phase. Additionally, the water phase sometimes contains dissolved contaminants which cause the water phase to be at least slightly acidic or alkaline. Accordingly, the preferred dye is substantially inert to modification by contact with moderately acidic or alkaline aqueous solutions.

Preferred fluorescent dyes have a quantum efficiency of at least about 0.5 percent. The quantum efficiency of a fluorescent material is defined as the number of photons emitted by the fluorescent material at the peak wavelength of the emission band divided by the number of photons absorbed at the peak wavelength of the absorption band by the fluorescent material. A relatively higher quantum efficiency tends to produce a greater amount of fluorescence radiation, which is easier to distinguish from any interfering radiation that may be present. Dyes having relatively higher quantum efficiencies are generally easier to detect and can be more effective when employed in lower concentrations.

The fluorescent dye preferably exhibits minimal absorbance in the visible range. Hydrocarbon consumers commonly associate certain colors with fine quality hydrocarbons. For example, a consumer accustomed to enjoying a crystal clear gasoline might be reluctant to purchase a gasoline tinged by a colored dye.

Also, certain commercial hydrocarbons presently contain visibly colored dyes as part of a widely established distribution scheme. Fluorescent dyes which do not absorb appreciably in the visible region can be employed simultaneously with such colored dyes without altering the established scheme of visibly colored hydrocarbons.

For tagging hydrocarbons that may be ultimately utilized as fuel, it is desirable that the fluorescent dyes contain no unnecessary metals, halogens or sulfur which might contribute to air pollution as byproducts of combustion. Preferably, the fluorescent dyes contain essentially no metals, halogens or sulfur. More preferably, the fluorescent dyes are composed essentially of carbon, hydrogen, oxygen, and nitrogen.

The fluorescent dyes must be relatively stable in the presence of components which are likely to be present in mixtures containing the tagged hydrocarbon. The fluorescent dye must be relatively inert in the presence of additives such as, for example, deposit control additives, anti-oxidant additives and detergent additives.

The fluorescent dyes of the present invention are detectable at comparatively low threshold concentrations, and can be employed at concentrations which obviate problems inherent in other hydrocarbon marking systems. The fluorescent dyes of the present invention are distributed in the tagged hydrocarbons at concentrations of about 0.01 to about 1,000 ppb by weight, preferably about 0.1 to about 500 ppb, most preferably about 1 to about 100 ppb. For purposes of comparison, one conventional red dye must be employed at dosages of 25 to 100 ppm in a hydrocarbon of interest in order to permit visual detection of that hydrocarbon as a five percent component of a hydrocarbon mixture. Such relatively high concentrations of red dye create objectionable solid deposits in internal combustion engines, unlike the parts per billion dye concentrations employed in the present invention.

The method also comprises passing radiation in the fluorescent band along a fluorescence path emanating from the target chamber. The fluorescence path may be simply a volume of space which is unobstructed in the sense that it is substantially transparent to radiation in the fluorescent band. Alternatively, the fluorescence path may be adjusted, focused or guided as by mirrors, lenses, prisms or internal surfaces of optical fibers.

The fluorescence path extends from the target chamber to a detector which is capable of detecting the presence of a predetermined amount of the fluorescence radiation. Upon detecting the presence of the predetermined amount, the detector produces a detection signal which preferably gives rise to a visible readout signal or an appropriate alarm. Suitable detectors, such as silicon photodiodes, are described above.

A proximal portion of the excitation path located adjacent the target chamber is herein defined as a final portion of the excitation path. A distal portion of the fluorescence path located adjacent the target chamber is designated an initial portion. In order to minimize the amount of excitation radiation which may be reflected, diffracted, or otherwise scattered so as to reach the detector, it is preferred that the final portion of the excitation path form about a ninety degree angle to the initial portion of the fluorescence path.

Moreover, it is especially desirable to shield the detector from radiation in the excitation band by means of a shield plate or a wavelength selective filter. The shield plate can include, for example, a generally planar slab material opaque to the excitation radiation which defines a relatively small aperture permitting fluorescence radiation to pass along a predetermined route. The route can be oriented in a direction which excitation radiation and any other interfering radiation is unlikely to travel.

Similarly, the wavelength selective filter shields the detector by blocking the passage of radiation outside of the fluorescent band, while passing radiation having wavelengths in the fluorescent band. The selective filter can be a bandpass filter, a cut-on filter, a prism, or an interference filter. The cut-on filter, which is also known as a high wavelength pass filter, is presently preferred.

In still another aspect, the invention is a method for detecting the presence of a tagged gasoline dispersed in a liquid. The hydrocarbon is tagged by blending with an appropriate amount of a suitable fluorescent dye, as described above. The liquid can be located, for example, in a storage vessel or a transfer pipe. Apparatus adapted to carry out the method are described below.

The method comprises generating radiation in an excitation band. The radiation includes wavelengths in the preferred ranges set forth above and describes an excitation path from an excitation source to a terminus. Preferably, the excitation path is guided along the excitation path by a delivery fiber optic conduit. For the present purposes, a fiber optic conduit is defined as one or more individual optical fibers.

The method further comprises immersing a submersible head into the liquid. The head includes a distal portion of the excitation path and is adapted to irradiate a target volume located in the excitation path. The target volume communicates with the liquid so as to become filled by the liquid when the head is immersed.

During operation, the liquid in the target volume is irradiated by radiation in the excitation band at an intensity sufficient to excite the fluorescent dye to emit. Fluorescence radiation emanates from the fluorescent dye and describes a florescence path extending to a terminus at a detector, as described above, which produces a detection signal.

The detector can be immersed in the liquid along with the head. However, it is preferred that a return fiber optic conduit guide the fluorescent path to a relatively protected place where the detector is located so that the detector need not be immersed in the liquid in order to detect the tagged hydrocarbon.

In an additional aspect, the invention is a method for tagging a hydrocarbon, such as a gasoline, for subsequent detection or identification. The method comprises blending a fluorescent dye, as described above, with the hydrocarbon at a concentration of about 0.01 to about 1000 parts per billion by weight. The blending can be accomplished by, for example, stirring, agitating, jet mixing, pumping or recirculating the fluorescent dye with the hydrocarbon. Preferably, an intermediate blend is prepared by first mixing the fluorescent dye with a carrier fluid, such as toluene or a portion of the hydrocarbon, which dissolves the fluorescent dye readily yet is not considered objectionable in the final blend. The intermediate blend facilitates in measuring and distributing the components of the final blend.

Preferably, the dye is substantially soluble in the hydrocarbon and essentially insoluble in water, as the water might otherwise leach the dye from the tagged hydrocarbon and prevent subsequent detection. Fluorescent dyes selected from the group consisting of naphthalocyanine dye, phthalocyanine dye, cyanine dye, methine dye, croconium dye and squarylium dye are recommended, especially those which absorb radiation having wavelengths of about 600 to about 2,500 nanometers and, thereafter, emit radiation in approximately the same range or at slightly greater wavelengths.

In yet another aspect, the invention is an apparatus for detecting the presence of a fluorescent dye in a hydrocarbon sample. Referring now to FIG. 1, the apparatus 10 comprises a sample receiver 12, preferably constructed of a relatively inert material that does not tend to scatter radiation. One example of a suitable material is a polymer commercially available under the trademark Delrin. Preferably, the sample receiver is a monolith defining an elongated target chamber 14 which communicates with an external surface of the sample receiver 12 and is adapted to permit insertion of a hydrocarbon sample, such as a gasoline sample, into the target chamber. More preferably, the target chamber 14 is also adapted to permit the entry of a relatively transparent sample container (not shown) which holds the hydrocarbon sample as it is inserted into the target chamber 14.

The sample receiver 12 additionally defines an excitation port 16 which communicates with the sample Receiver 12 and, preferably, also communicates with an external surface of the sample receiver 12. More preferably, the excitation port 16 is elongated and is oriented axially to the target chamber 14. The excitation port 16 is adapted to house an excitation source 18 which is suitable for generating radiation in an excitation band including wavelengths of about 600 to about 2,500 nanometers, preferably about 630 to about 830 nanometers, and most preferably about 700 to about 800 nanometers. It is especially preferred that the excitation source is a laser diode.

A battery, such as a nine-volt battery 21, having two terminals is connected at one of the terminals to a signal ground 19 by a ground lead 20. When a switch 23 is closed, electricity flows from the other of the terminals of the battery 21 through power leads 22 and 24, junction 25, and power lead 26 to arrive at an excitation source driver, such as the laser diode driver 27 illustrated in FIG. 1.

The driver 27 is a well-known device, usually commercially available, which supplies power and provides feedback control to a laser diode. The driver 27 is connected to the signal ground 19 by a ground lead 28. Power leads 30 and 31 extend from the driver 27 to an excitation source 18, preferably a laser diode, and more preferably a continuous GaAlAs laser diode as depicted in FIG. 1. In the excitation source 18, electrical energy is converted to electromagnetic radiation, preferably essentially monochromatic and coherent, which describes an excitation path 32 extending from the excitation source 18 to a terminus 33 located adjacent or within the target chamber 14.

When the excitation source 18 is a laser diode, a control lead 29 extends from the driver 27 to a photodiode which is conventionally incorporated in the laser diode. A signal from the incorporated photodiode is used as feedback to control the laser diode output in a desirable energy range.

Also defined by the sample receiver 12 is a fluorescence port 34 which communicates with the target chamber 14 and, preferably, with an external surface of the sample receiver 12. More preferably, the fluorescence port 34 is elongated and oriented axially to the target chamber 14. The fluorescence port 34 houses a detector 35, which is preferably a silicon photodiode capable of producing an output voltage signal upon detecting radiation in the fluorescent band. The detector 35 is connected to a signal conditioning amplifier circuit board 37, described below, via signal leads 36 and 38.

The target chamber 14 is adapted for receiving and exposing a gasoline sample to radiation, preferably, by communicating with one of the external surfaces and by defining the ports 16 and 34. Radiation in the fluorescent band emitted by a sample in the target chamber 14 describes a fluorescence path 40 which extends from target chamber 14 to a terminus 42 at the detector 35.

It is highly recommended that precautions be taken to minimize the amount of radiation in the excitation band which can travel from the excitation source 18 to the detector 35. For example, a shield plate 44 is preferably located in the fluorescence path. The shield plate 44 is constructed of a material which is substantially opaque to radiation in the excitation band and defines a relatively small aperture 46 which is, preferably, oriented at approximately 90° to the excitation path.

Also, a wavelength selective filter 47 is located in the fluorescence path 40 so that radiation from the target chamber 14 must pass through the selective filter 47 to reach the detector 35. The selective filter is a band pass filter, a cut-on filter, or an interference filter, preferably a cut-on filter. The selective filter 47 is intended to be substantially opaque to radiation having wavelengths less than the wavelengths of the fluorescent band while being substantially transparent to radiation in the fluorescent band.

The circuit board 37 is powered by the battery 21, directly through the junction 25, power leads 48 and 50, and a junction 49, and indirectly through a voltage regulator 52 and power leads 51 and 54. The circuit board 37 and the voltage regulator 52 are connected to the signal ground 19 by ground leads 55 and 53, respectively.

By means of well-known signal conditioning and amplifier techniques, the circuit board 37 receives a voltage signal in the form of a voltage difference between the signal leads 36 and 38, converts the voltage signal to a current, amplifies the current, and compares the amplified current to a predetermined value which corresponds to a predetermined intensity of radiation in the fluorescent band at the detector 35.

Optionally, the amplified current can be conditioned by, for example, scaling and adding offsets, and directed to a voltage readout (not shown). The voltage readout provides a direct indication of the concentration of the dye in the sample.

If the amplified current is determined to be about equal to or greater than the predetermined value, electricity is transmitted through an indicator 57, via leads 56 and 58. Preferably, the indicator 57 includes a light-emitting diode which lights up to indicate that the sample in the target Chamber 14 contains at least a predetermined minimum concentration of the fluorescent dye.

Alternatively, if the amplified current is less than the predetermined value, electricity is transmitted through an indicator 62, via leads 60 and 63 to indicate that the predetermined minimum concentration of the fluorescent dye is not present. Surprisingly, the predetermined value can be adjusted so that the indicator 57 lights up when a sample containing only a few percent by volume of the tagged gasoline is inserted into the target chamber 14.

Figure 2:
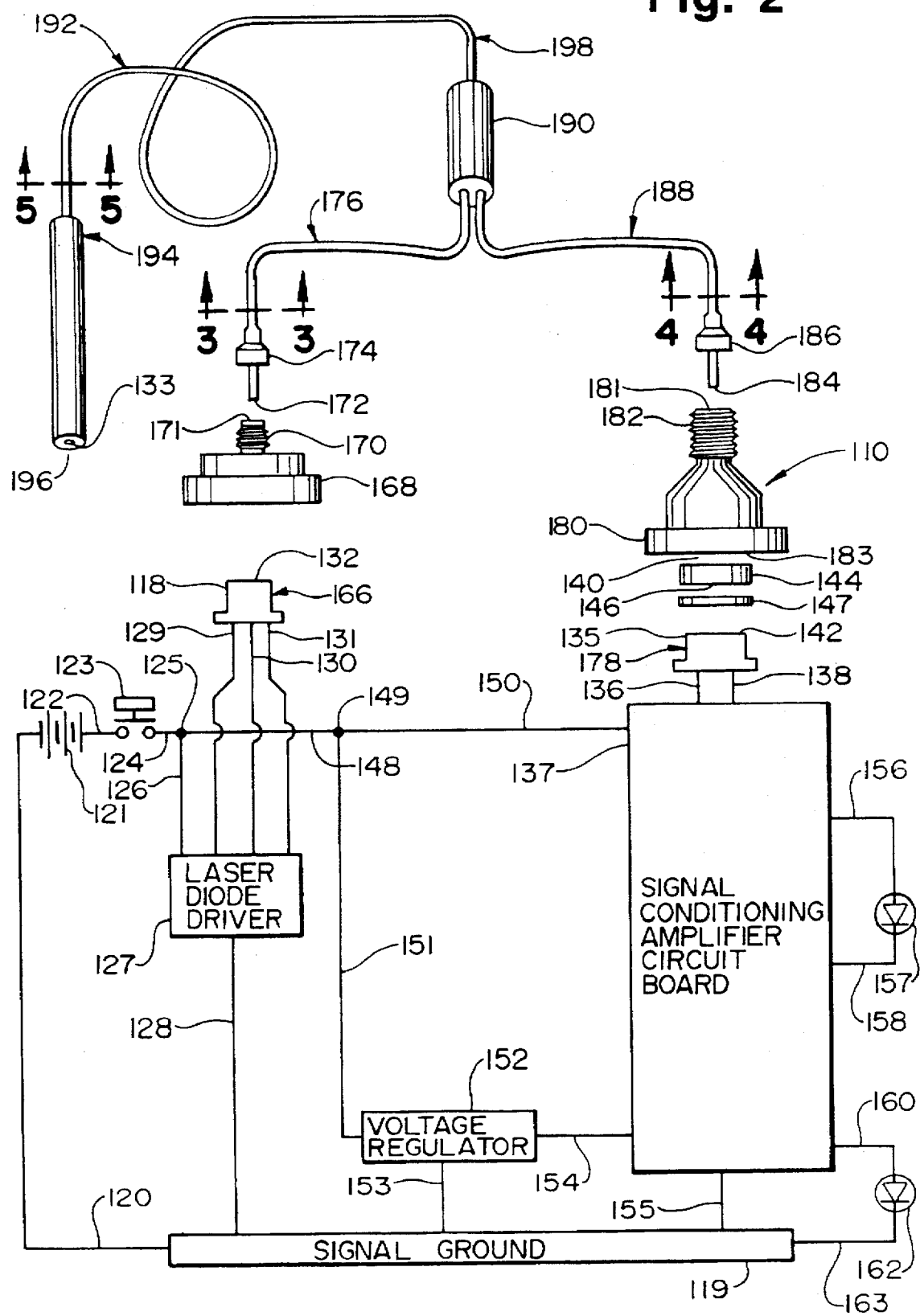
FIG. 2 is a schematic diagram of an apparatus for detecting the presence of a tagged gasoline dispersed in a liquid, with fiber optic conduits which are suitable for transmitting electromagnetic radiation shown in exploded perspective view.

In still another aspect, the invention is an apparatus 110 depicted in FIG. 2 for detecting the presence of a tagged gasoline dispersed in a liquid located, for example, in a storage tank or a transfer pipe. Regarding FIG. 2, elements which are substantially similar to elements depicted in FIG. 1 are assigned element numbers having values which are exactly one hundred units greater as compared to the element numbers of the similar elements in FIG. 1. For example, an excitation source 118 in FIG. 2 is substantially similar to the excitation source 18 in FIG. 1.

Referring now to FIG. 2, a generator assembly 166 includes the excitation source 118 and a laser diode driver 127, which controls the delivery of electrical power from a battery 121 to the excitation source 118. A connector 168 defining an aperture 171 therethrough and having screw threads 170 situated about the aperture 171 receives and aligns the excitation source 118 in an orientation that permits electromagnetic radiation generated in the excitation source 118 to travel through the aperture 171. Accordingly, when the generator assembly 166 is operating, an excitation path 132 originates at the excitation source 118 and extends through the aperture 171 defined by the connector 168.

Figure 3:
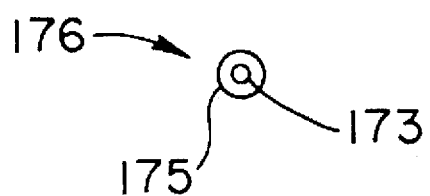
FIG. 3 is a cross-section of a delivery fiber optic conduit, relating to section line 3—3 of FIG. 2.

Referring briefly to FIG. 3, an elongated delivery fiber optic conduit 176 includes at least one optical fiber, such as an optical fiber 173, within a protective sheath 175. The delivery conduit 176 is illustrated in FIG. 3 as a cross-section corresponding to section line A—A of FIG. 2. Returning to FIG. 2, the delivery conduit 176 has a proximal end defining a tip 172 adapted to pass through the aperture 171. A gland nut 174 surrounds the delivery conduit 176 and engages the screw threads 170 to attach the tip 172 securely in the excitation path 132. Preferably, the tip 172 abuts excitation source 118.

A detector assembly 178 includes a detector 135, signal leads 136 and 138, and a signal conditioning and amplifier circuit board 137. A connector 180 defines an aperture 181 therethrough and a recess 183 communicating with the aperture. Screw threads 182 are situated about the aperture. The connector 180 receives the detector 135, a shield plate 144 and a wavelength selective filter 147 into the recess 183 with the detector 135 opposite the aperture 181.

Figure 4:
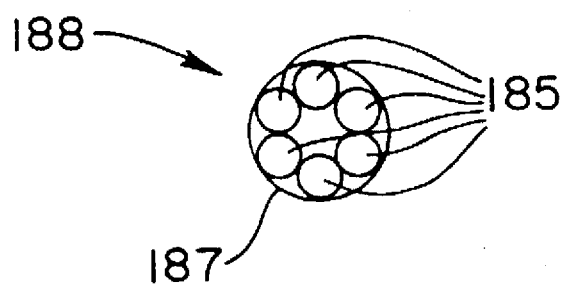
FIG. 4 is a cross-section of a return fiber optic conduit including several optical fibers, relating to section line 4—4 of FIG. 2.

An elongated return fiber optic conduit 188 includes at least one optical fiber, preferably a plurality of optical fibers such as the optical fibers 185, located within a protective sheath 187 depicted in cross-section in FIG. 4. Section line B—B of FIG. 2 corresponds to a cross-sectional view illustrated in FIG. 4. Returning again to FIG. 2, the return conduit 188 has a proximal end defining a tip 184 adapted to pass through the aperture 181. A gland nut 186 about the return conduit 188 engages the screw threads 182 to attach the tip 184 opposite the detector 135. A fluorescence path 140 extends through the return conduit 188 to a terminus 142 at the detector 135. Preferably, the tip 184 faces the detector 135 when the gland nut 186 is fastened.

Figure 5:
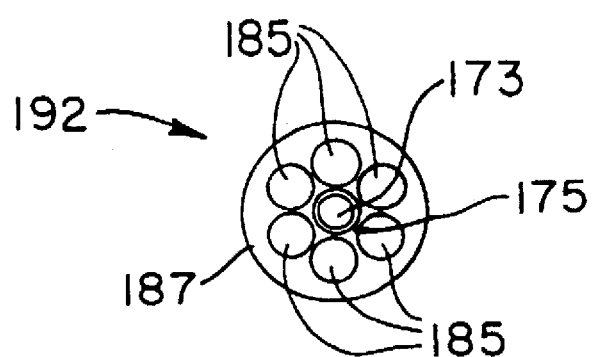
FIG. 5 is a cross-section of a bifurcated fiber optic bundle including return optical fibers and a delivery optical fiber, relating to section line 5—5 of FIG. 2.

The delivery conduit 176 and the return conduit 188 join at a bifurcation junction 190 to form a bifurcated fiber optic bundle 192, depicted in cross-section in FIG. 5. FIG. 5 is a cross-sectional view corresponding to section line C—C of FIG. 2. The bundle 192 contains a portion of the optical fiber 173 and of the sheath 175, as well as portions of the optical fibers 185 and of the sheath 187. Preferably, the optical fibers 185 are arranged circumferentially about the optical fiber 173.

Preferably, all of the optical fibers 173 and 185 extend continuously from the tips 172 and 184 through an armor-clad submersible head 194 to terminate opposite a target volume 196. The submersible head 194 is impervious to submersion in hydrocarbons and is adapted to resist breaking under the forces normally encountered upon being lowered into a hydrocarbon storage vessel. The excitation path 132 emerges from the distal end of the optical fiber 173 into the target volume 196. The target volume 196 is defined as the volume in which a portion of the excitation path 132 coincides with a portion of the fluorescence path 140.

During operation, the target volume 196 is occupied by a hydrocarbon liquid which partially absorbs radiation emanating from the optical fiber 173. When a tagged hydrocarbon which contains a fluorescent dye as described above is present in the target volume 196, fluorescence radiation is emitted by the dye and received into the optical fibers 185. The optical fibers guide the received fluorescence radiation along the fluorescence path 140, which originates at the emitting fluorescent dye molecules, to the detector 135. A detection signal is generated by the circuit board 137, as described above.

The following Examples are presented in order to better communicate the invention. The Examples are not intended to limit the scope of the invention in any way.

EXAMPLE 1

Figure 6:
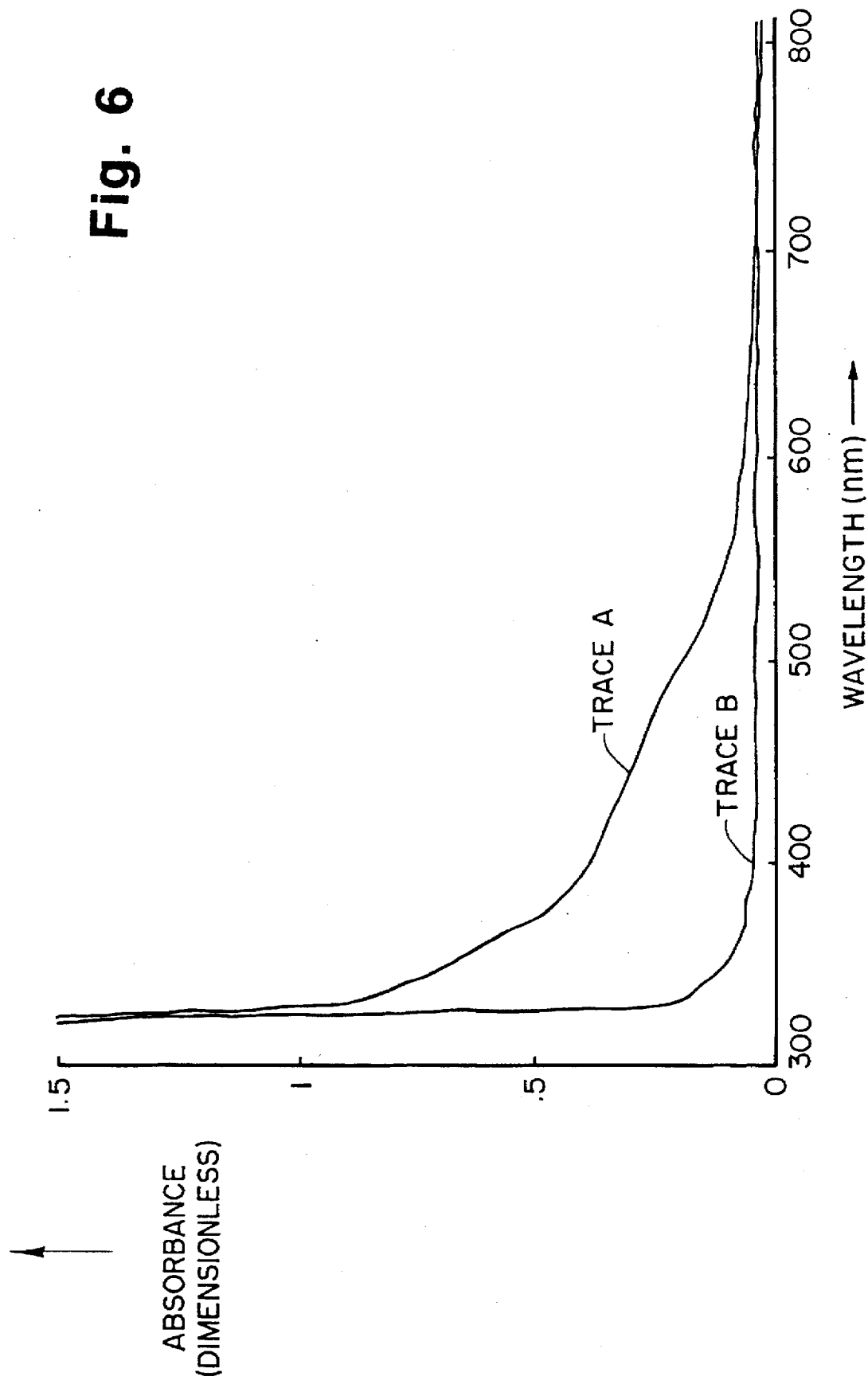
FIG. 6 is a graph illustrating natural absorbance in the ultraviolet, visible and near infrared spectral regions as functions, designated Trace A and Trace B, of incident radiation wavelength for regular and premium gasoline samples, respectively.

Referring now to FIG. 6, Trace A depicts the absorbance of a naturally colored, regular-grade gasoline as a function of incident radiation wavelength. The absorbance is depicted in absorbance units, which is a dimensionless quantity defined as the product of molar absorbance times path length times concentration; the wavelength is shown in nanometers.

Inspection of Trace A reveals significant absorption in the visible range, from about 330 to about 650 nanometers. While the gasoline of Trace A contains no artificial dyes, it actually appears reddish to the human eye. Such visible coloration is apt to interfere with fluorescence detection of tagging dyes in the visible range, because the gasoline of Trace A can be expected to absorb at least a portion of any visible range excitation or fluorescence radiation which passes through the gasoline.

Further inspection reveals that the regular gasoline of Trace A absorbs strongly in the ultraviolet region, at wavelengths of about 330 nanometers or less. Accordingly, the natural absorbance of the Trace A regular gasoline is likely to interfere with any fluorescence detection of tagging dyes attempted in the ultraviolet range.

Trace B of FIG. 6 illustrates the absorbance of a relatively low-color, premium-grade gasoline as a function of incident light wavelength. The absorbance scale utilized with Trace A is also applied to Trace B, and the wavelength is again in nanometers. The gasoline of Trace B contains no dyes. To the contrary, the gasoline of Trace B is the product of a decolorizing and purification process intended to remove visible range color bodies as well as some aromatic hydrocarbon molecules.

The gasoline of Trace B appears crystal clear to the human eye, yet Trace B indicates absorbance below the visible range which is sufficiently strong to interfere with fluorescence detection of tagging dyes in the ultraviolet region. Significantly, both Trace A and Trace B show comparatively little absorbance in the wavelength region of about 600 or more nanometers.

EXAMPLE 2

Three gasoline samples were each blended with 10 ppm by weight of one of three artificial visible dyes which are currently utilized in the marketplace. The dyes appeared as yellow, red and blue, respectively, to the human eye. The blended samples were irradiated with radiation of the ultraviolet, visible and infrared spectral regions which included various wavelengths ranging from 300 to 800 nanometers. Simultaneously, the absorbances of the samples as functions of incident radiation wavelength were measured and recorded. The absorbance data are presented graphically as FIG. 7.

Figure 7:
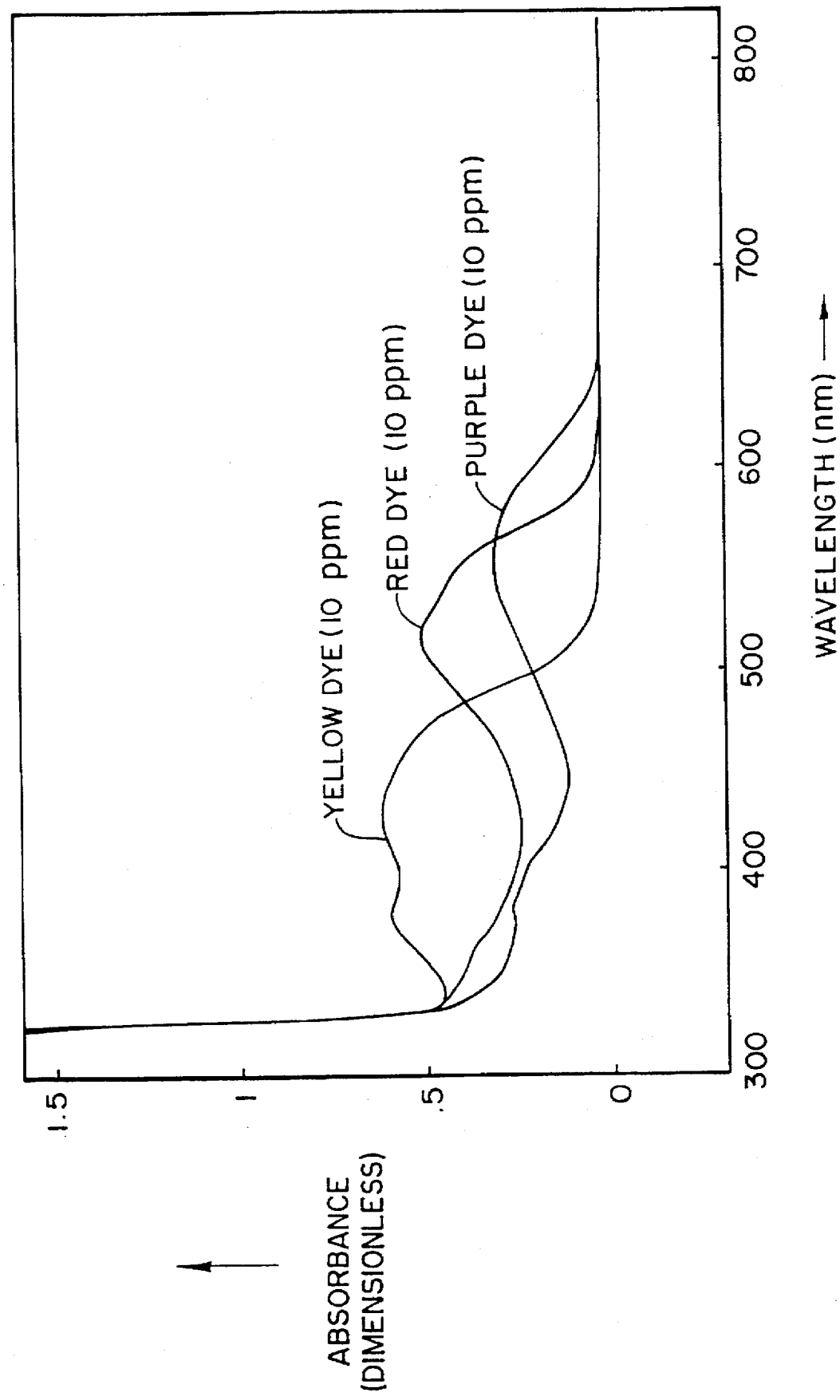
FIG. 7 is a graph illustrating absorbance in the ultraviolet, visible and near infrared spectral regions for three gasoline samples, each containing 10 ppm of one of three artificial visible dyes commonly utilized in the marketplace.

The data of FIG. 7 indicates that additional dyes which absorb or fluoresce in the ultraviolet or visible spectral regions are, when present in the same sample, subject to significant interference from currently employed visible dyes. Fluorescent dyes operating primarily in the ultraviolet or visible regions are at an especial disadvantage, as the visible dyes tend to absorb both excitation radiation and fluorescence radiation in those spectral regions.

EXAMPLE 3

Figure 8:
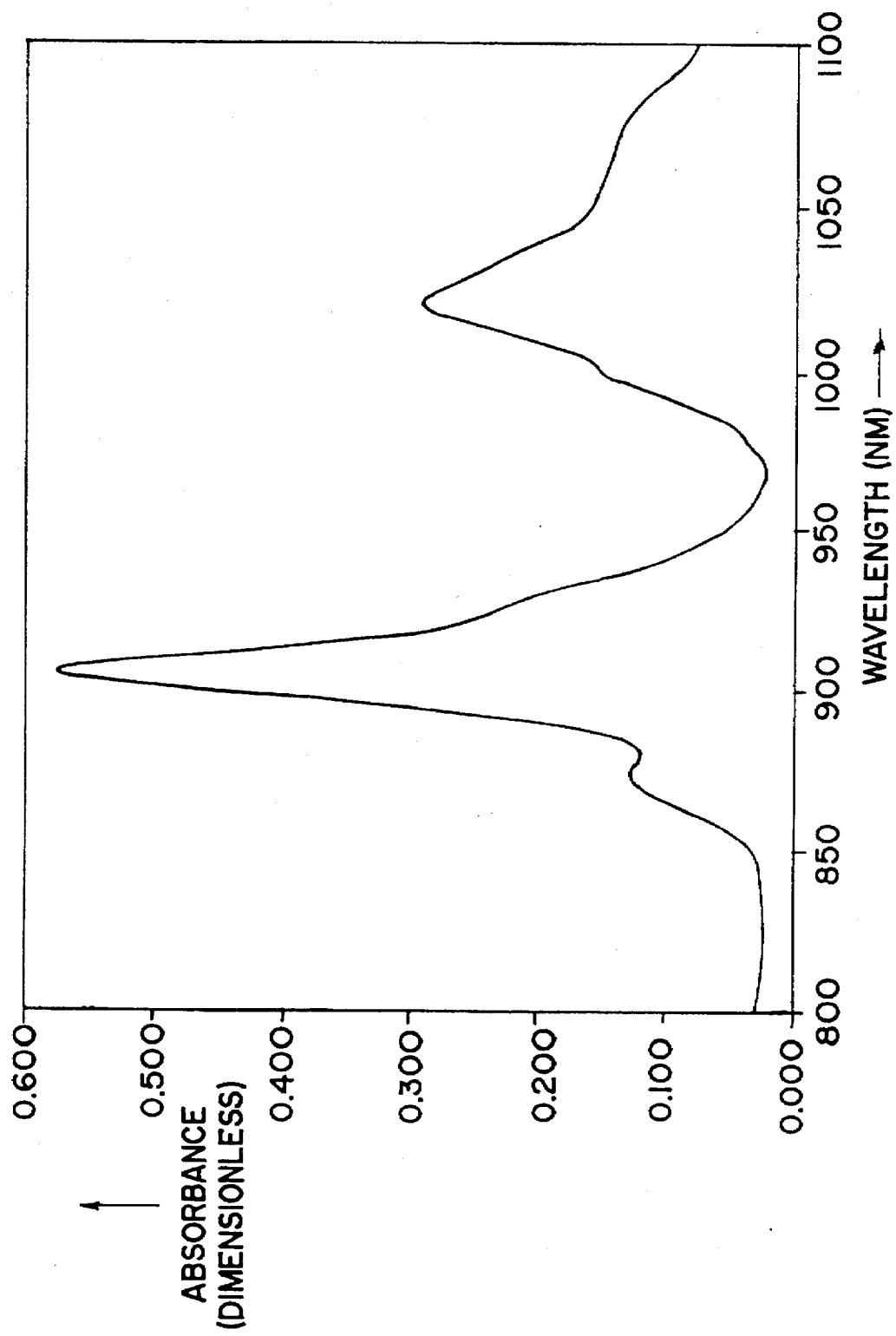
FIG. 8 is a graph presenting absorbance in the near infrared spectrum as a function, designated Trace C, of incident light wavelength for a gasoline sample.

Turning now to FIG. 8, Trace C presents absorbance for a third gasoline in the wavelength region of about 800 to 1,100 nanometers. The general shape of Trace C is believed to be typical for gasolines, generally. Absorption peaks can be discerned in Trace C, at about 875 and about 910 nanometers, which are associated with a third overtone of carbon to hydrogen vibrational bond stretching absorption typically observed in gasolines. The absorption peaks, circa 1,020 nanometers, are near infrared combinations of two or more vibrational bond stretching absorbances and their overtones. FIG. 8 provides evidence that gasolines naturally absorb less in the range of about 800 to 1,100 nanometers than, for example, do gasolines in the ultraviolet region. More specifically, the data of FIG. 6, FIG. 7 and FIG. 8 taken together indicate that radiation having wavelengths of about 630 to about 830 is especially preferred for fluorescent detection of tagging dyes in gasolines, and in hydrocarbon mixtures containing gasolines.

EXAMPLE 4

Figure 9:
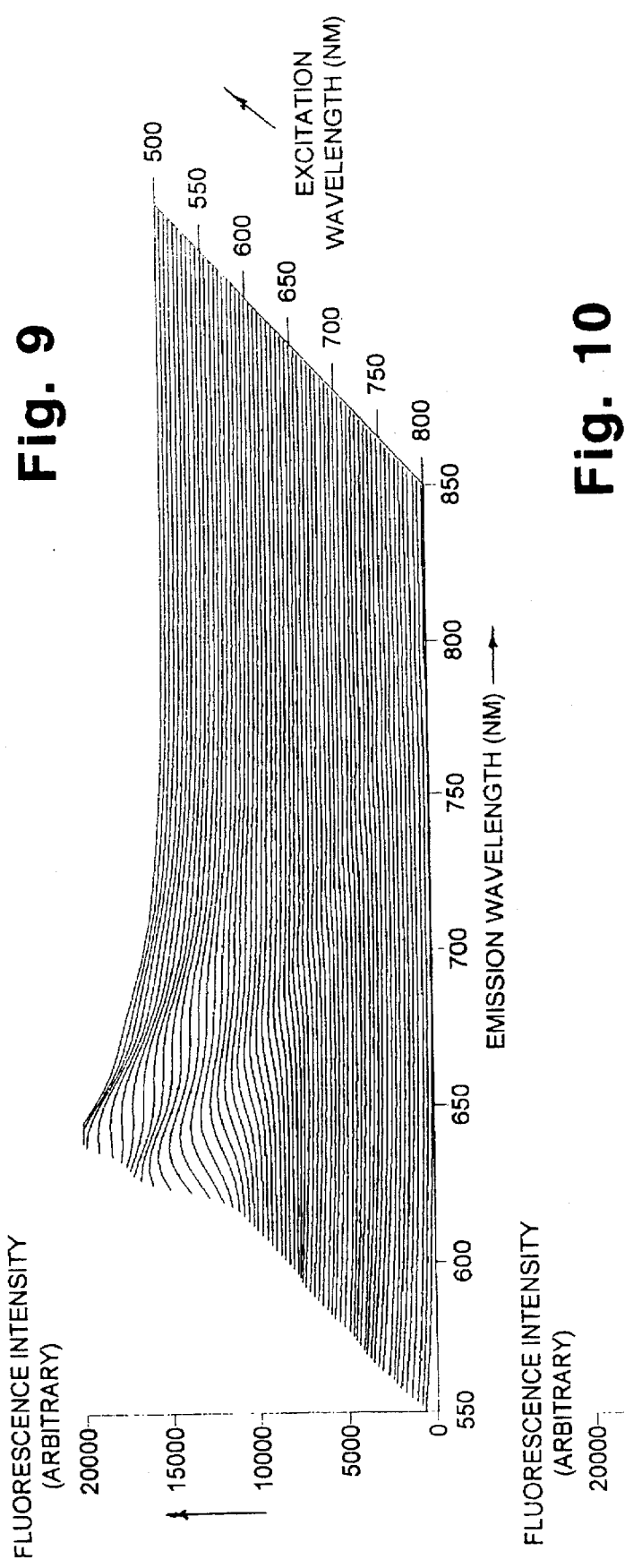
FIG. 9 is a two dimensional projection of a three dimensional surface corresponding to a fluorescence response observed for a naturally colored regular grade gasoline containing no artificial dyes.

FIG. 9 is a two dimensional projection, sometimes called a hidden line view, of a three dimensional surface which conveys the fluorescence response of the naturally colored regular grade gasoline described above with reference to Trace A of FIG. 6. In FIG. 9, the oblique axis shows the excitation radiation wavelengths, ranging from 550 to 800 nanometers, utilized serially to stimulate the premium grade gasoline to fluorescence. The horizontal axis represents the wavelengths of fluorescence radiation, ranging from 550 to 850 manometers, observed as a result of stimulation by the corresponding excitation radiation wavelengths. The vertical axis depicts the fluorescence intensity of the observed fluorescent radiation drawn to an arbitrary scale for each excitation wavelength and fluorescence wavelength combination.

A ridge which appears to cut diagonally across the surface depicted in FIG. 9 is believed to be caused by scattered source radiation, known as Rayleigh scattering radiation, which travelled to the detector without being absorbed by the gasoline and caused a detection signal. The Rayleigh scattering signal is not due to fluorescence but is, rather, a type of background interference to be minimized.

FIG. 9 demonstrates that some gasolines are naturally fluorescent. For example, when the regular grade gasoline was stimulated by excitation radiation having a wavelength of 500 nanometers, fluorescence radiation having a wavelength of 550 nanometers was observed having a fluorescence intensity on the arbitrary scale of 5,700. As another example, excitation radiation having a wavelength of 750 nanometers stimulated the regular grade gasoline to emit fluorescence radiation having a wavelength of 800 nanometers with a fluorescence intensity of 110 according to the arbitrary scale. Although it is not evident in FIG. 9, the fluorescence of many gasolines is relatively stronger still in the low visible and ultraviolet regions.

The surface illustrated in FIG. 9 displays the natural excitation and fluorescence behavior of the regular gasoline alone, in the absence of any artificial dyes. Inspection of FIG. 9 indicates that the regular gasoline exhibits relatively little natural fluorescence at wavelengths over about 600 nanometers, and surprisingly little natural fluorescence in the range of about 650 to about 850 nanometers. The relative absence of natural gasoline fluorescence makes these ranges especially suitable for the detection of florescent dyes.

EXAMPLE 5

Figure 10:
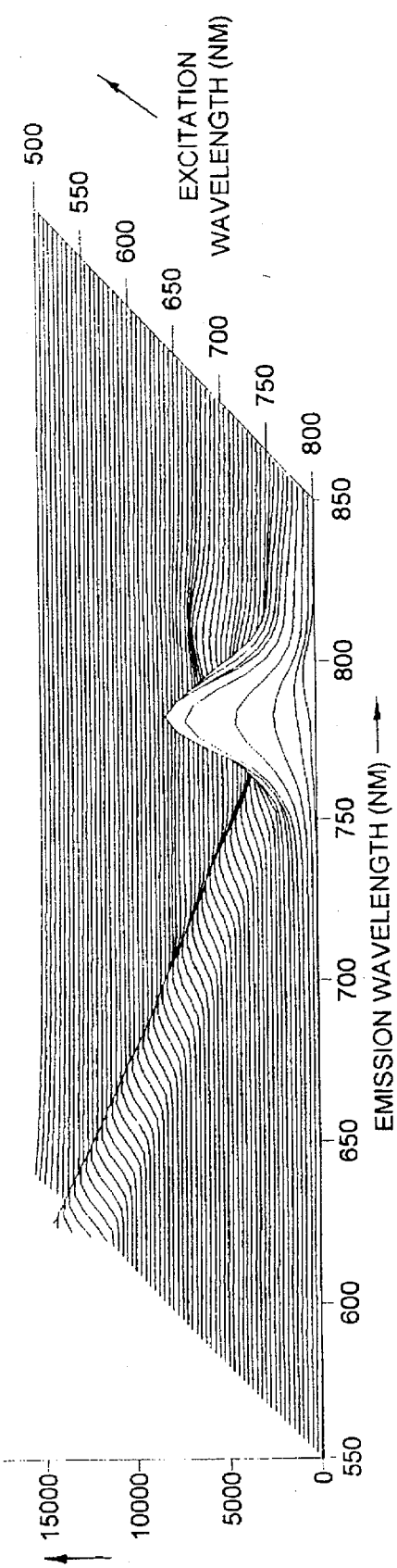
FIG. 10 is a two dimensional projection of a three dimensional surface corresponding to a fluorescence response observed for a relatively colorless premium grade gasoline containing a fluorescent dye which exhibits a fluorescence peak at 780 nanometers when excited by radiation at 775 nanometers.

FIG. 10 presents a two dimensional projection of a three dimensional surface representing the excitation and fluorescence response observed when the relatively colorless, premium grade gasoline of Trace B in FIG. 6 was tagged with a fluorescent dye and irradiated. The fluorescent dye, designated Dye I, was present in the premium grade gasoline at a concentration of 80 ppb by weight. Rayleigh scattering appears as a ridge which cuts diagonally across the projection.

An artificial fluorescence peak is clearly distinguishable at 780 nanometers. FIG. 10 demonstrates that a fluorescent dye situated in a proper region of the electromagnetic spectrum can stand out dramatically from interference and background radiation in a hydrocarbon, even at a concentration in the parts per billion range.

EXAMPLE 6

Figure 11:
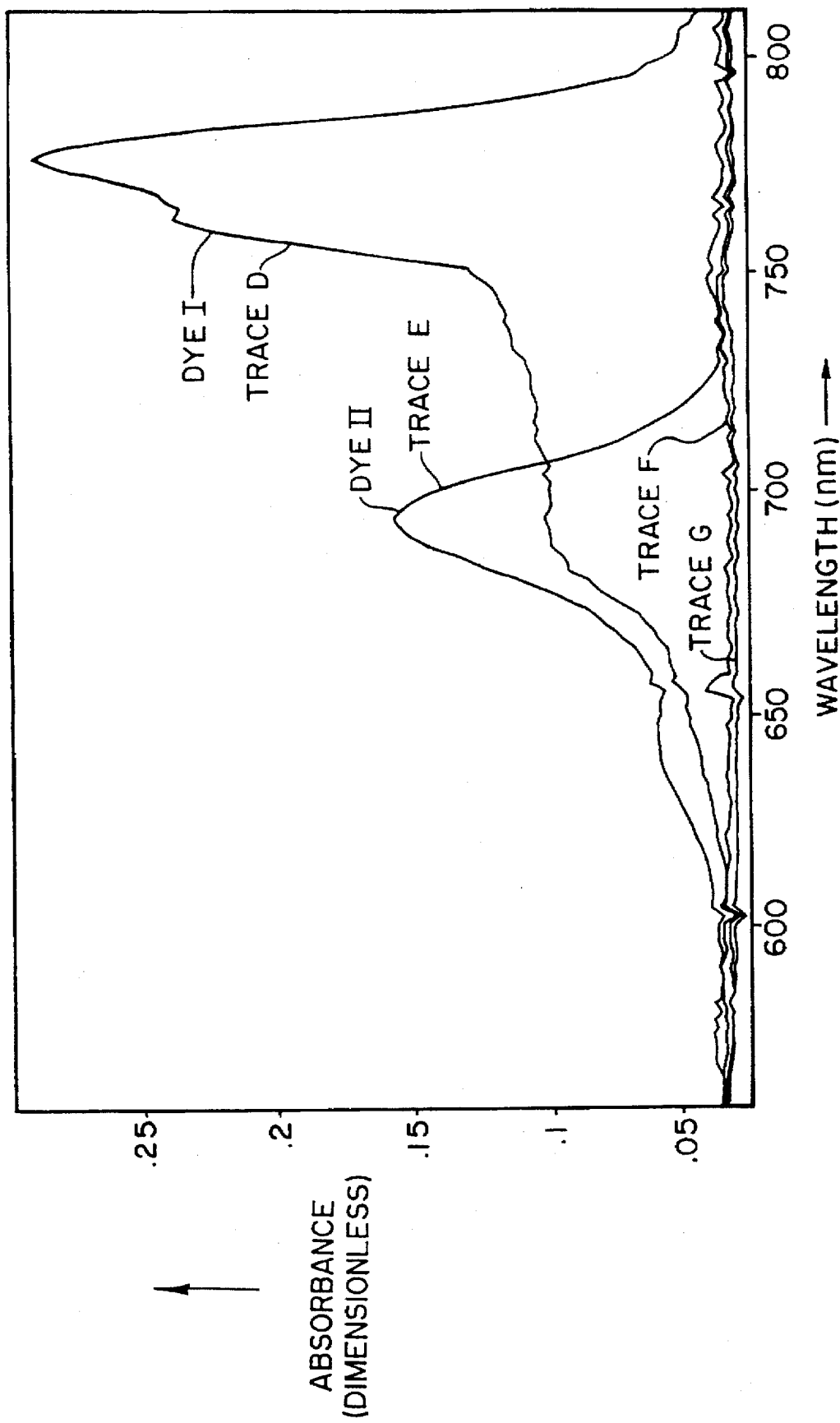
FIG. 11 is a graph depicting absorbance exhibited by gasoline samples containing Dye I and Dye II, designated Trace D and Trace E, respectively and depicting absorbance exhibited by similar gasoline samples containing no dye, designated Trace F and Trace G.

Practitioners will appreciate that each fluorescent dye composition exhibits highly individual absorption peaks and fluorescence peaks when dispersed in a given hydrocarbon. Referring now to FIG. 11, Trace D presents an absorption spectra exhibited by Dye I at various wavelengths when irradiated in the premium grade gasoline of Trace B at a concentration of approximately 300 parts per billion. Trace D indicates an absorption peak for Dye I at 775 nanometers.

Also in FIG. 11, Trace E illustrates an absorption spectra exhibited by Dye II when irradiated in the premium grade gasoline of Trace B at a concentration of approximately 170 parts per billion. Trace E indicates an absorption peak of 690 nanometers.

Trace F and Trace G depict absorption spectra of two undyed (blank) samples of the premium grade gasoline, for purposes of comparison.

As a whole, FIG. 11 demonstrates that fluorescent dyes exhibit absorption peaks, and that the absorption peaks are generally surrounded by absorption bands including wavelengths which are strongly absorbed by the fluorescent dyes. FIG. 11 also illustrates that fluorescent dyes can be selected which exhibit absorption peaks in the desirable spectral region of about 600 to about 2,500 nanometers, more specifically about 630 to about 830 nanometers. Additionally, it can be seen that the dyes employed are indeed strongly absorbing.

EXAMPLE 7

Figure 12:
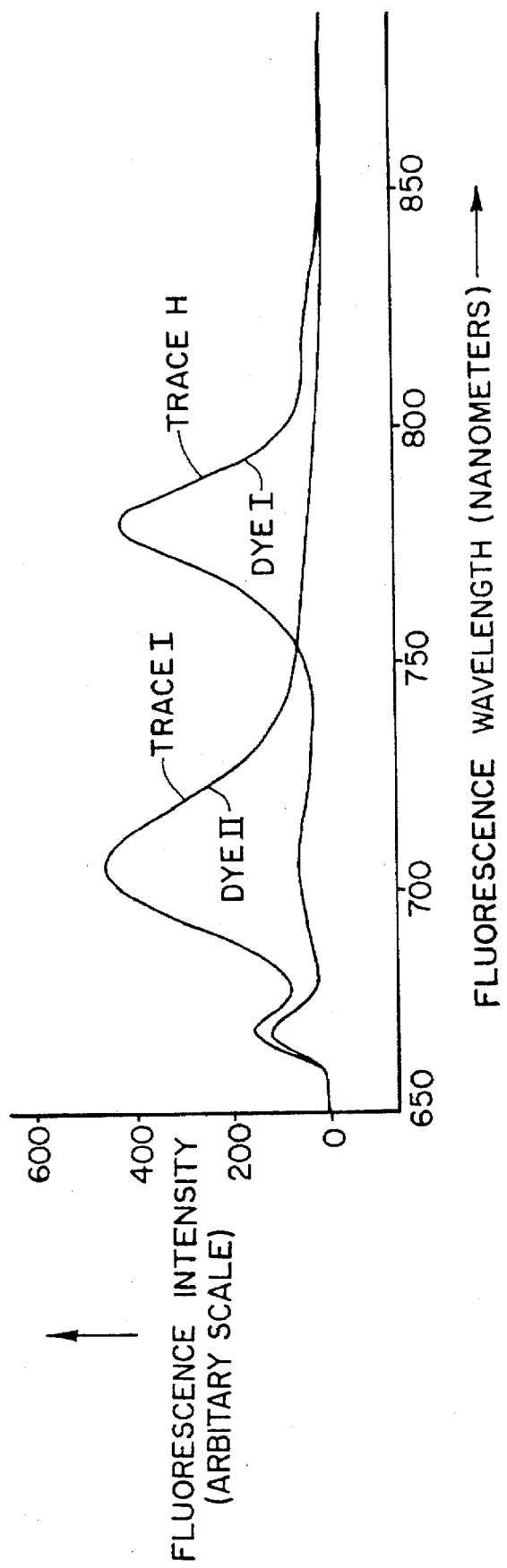
FIG. 12 is a graph depicting fluorescence intensity exhibited by gasoline samples containing Dye I and Dye II as functions designated Trace H and Trace I, respectively, of incident light in the wavelength range of 650 to 850 nanometers.

Trace H and Trace I of FIG. 12 depict the fluorescence spectra of Dye I and Dye II, respectively, observed when the dyes were blended with samples of the low color, premium grade gasoline of Trace B and stimulated with radiation in a relatively narrow band having a peak wavelength of 670 nanometers. Trace H, observed at a 650 ppb concentration of Dye I, indicates a fluorescence peak at 780 nanometers. Trace I, observed at a concentration of 170 ppb of Dye II, indicates a fluorescence peak at 710 nanometers.

FIG. 12 demonstrates that fluorescent dyes can be selected which exhibit fluorescence peaks in the desirable spectral region of about 600 to about 2,500 nanometers, more specifically about 650 to about 850 nanometers. The traces of FIG. 12 also serve to clarify the manner in which fluorescence radiation is commonly grouped in a fluorescent band surrounding the fluorescence peak.

EXAMPLE 8

Approximately aliquot portions of a fluorescent dye in accordance with the present invention were blended with samples of a premium grade gasoline at various concentrations ranging from 43 to 248 ppb by weight. Additionally, one sample of the gasoline received no fluorescent dye. The premium grade gasoline was described above with reference to Trace B of FIG. 6. The fluorescent dye was Dye I, described above with reference to Trace D of FIG. 11; utilizing an apparatus substantially similar to the apparatus 10 of FIG. 1, the samples were subsequently excited by 3 miliwatts of diode laser radiation having a peak wavelength of 750 nanometers. Upon detecting radiation emitted by the samples, a photodiode produced a voltage signal which was amplified, as described above, and measured. The data collected are presented below, as Table I.

TABLE I

| Sample | Dye Concentration (ppb) | Amplified Signals (Volts) |
|---|---|---|
| A | 0.00 | 0.091 |
| B | 43.4 | 0.388 |
| C | 86.0 | 0.671 |
| D | 128. | 0.957 |
| E | 169. | 1.225 |
| F | 209. | 1.55 |
| G | 248. | 1.785 |

The amplified voltage signals presented in Table I are quite linear with respect to the fluorescent dye concentration. Accordingly, the data of Table I was utilized to calculate the slope of the amplified signals as a linear function of the dye concentration. Additionally, data was collected for 16 replicate blank gasolines to determine the standard deviation.

tests, were measured after amplification in the detection circuitry and are listed in Table II, below.

TABLE II

| Brand | Metro Area | Oxygenate | Undyed 750 nm Voltage | Undyed 670 nm Voltage | Dye 1 750 nm 25 ppb Voltage | Dye 2 670 nm 100 ppb Voltage |
|---|---|---|---|---|---|---|
| Amoco | Baltimore | None | 0.001 | 0.159 | 0.270 | 0.873 |
| Amoco | Charlotte, NC | None | 0.001 | 0.158 | 0.282 | 0.870 |
| Amoco | New York | MTBE | 0.001 | 0.157 | 0.284 | 0.875 |
| Shell | Chicago | MTBE | 0.001 | 0.163 | 0.240 | 0.861 |
| Shell | Detroit | None | 0.001 | 0.159 | 0.227 | 0.872 |
| Shell | Indianapolis | MTBE | 0.001 | 0.162 | 0.251 | 0.886 |
| Mobil | Miami | MTBE | 0.001 | 0.165 | 0.202 | 0.833 |
| Mobil | Washington, DC | TAME/ MTBE | 0.001 | 0.168 | 0.231 | 0.854 |
| Mobil | Chicago | None | 0.001 | 0.158 | 0.244 | 0.849 |
| Mobil | Madison | None | 0.001 | 0.163 | 0.243 | 0.849 |
| Mobil | South Bend | Ethanol | 0.001 | 0.161 | 0.223 | 0.881 |
| Texaco | Miami | MTBE | 0.001 | 0.162 | 0.232 | 0.839 |
| Texaco | New York | TAME/ MTBE | 0.001 | 0.164 | 0.214 | 0.851 |
| Texaco | Kansas City, Mo | None | 0.001 | 0.165 | 0.253 | 0.865 |
| Texaco | Omaha | None | 0.001 | 0.165 | 0.251 | 0.885 |
| BP | Cincinnati | None | 0.001 | 0.159 | 0.212 | 0.834 |
| BP | Cleveland | Ethanol | 0.001 | 0.161 | 0.214 | 0.885 |
| BP | Memphis | MTBE | 0.001 | 0.162 | 0.238 | 0.839 |
| Exxon | New York | TAME/MTBE | 0.001 | 0.159 | 0.239 | 0.845 |
| Exxon | Philadelphia | MTBE | 0.001 | 0.159 | 0.27 | 0.853 |
| Citgo | Chattanooga | TAME/MTBE | 0.001 | 0.160 | 0.240 | 0.881 |
| Citgo | Philadelphia | MTBE | 0.001 | 0.159 | 0.251 | 0.839 |
| Citgo | Pittsburgh | Ethanol | 0.001 | 0.164 | 0.217 | 1.576 |
| Citgo | Detroit | None | 0.001 | 0.162 | 0.214 | 0.845 |
| Citgo | St. Louis | Ethanol | 0.001 | 0.167 | 0.206 | 0.903 |
| Phillips | Charlotte, NC | TAME/MTBE | 0.001 | 0.163 | 0.215 | 0.806 |
| Phillips | Chicago | None | 0.001 | 0.162 | 0.257 | 0.868 |
| Phillips | Omaha | None | 0.001 | 0.160 | 0.249 | 0.848 |
| Phillips | South Bend | Ethanol | 0.001 | 0.163 | 0.230 | 0.880 |
| Sunoco | Cincinnati | Ethanol | 0.001 | 0.161 | 0.229 | 0.901 |
| Sunoco | Pittsburgh | None | 0.001 | 0.158 | 0.245 | 0.839 |
| Sunoco | Washington, DC | MTBE | 0.001 | 0.158 | 0.251 | 0.879 |
| Sunoco | South Bend | None | 0.001 | 0.159 | 0.253 | 0.882 |
| Chevron | Cincinnati | MTBE | 0.001 | 0.160 | 0.268 | 0.895 | tion of the blank and, based on that information, to estimate the detection limit of this analysis technique.

Employing the definition for limit of detection (LOD) adopted by the International Union of Pure and Applied Chemists, LOD=$3S_b$/slope where $S_b$ is standard deviation, the limit of detection for this analysis is 0.1 parts per billion by weight. The estimate is consistent with a 99.7% statistical certainty that the fluorescent dye designated Dye I in the premium gasoline is detectable at 0.1 ppb concentration.

EXAMPLE 9

An apparatus substantially similar to the apparatus 10 depicted in FIG. 1 was employed to detect various gasoline samples, each containing one of two fluorescent dyes at predetermined concentrations or, alternatively, containing no fluorescent dye. The samples were excited by laser radiation having a wavelength of 750 nanometers. Fluorescence radiation was detected by a photodiode which was screened by a cut-on filter having a cut-on wavelength of 790 nanometers. The photodiode produces a voltage signal when exposed to radiation passing through the cut-on filter. At another time, the samples were excited by laser radiation at a wavelength of 670 nanometers giving rise to fluorescence radiation which reached the photodiode by passing through a cut-on filter having a cut-on wavelength of about 697 nanometers. The voltages from the photodiode, in both The data presented in Table II above is a representative portion of data collected by testing over 180 samples of gasoline with the two dyes. Inspection of the data in Table II reveals that concentrations of fluorescent dye as low as 25 parts per billion by weight can be reliably detected in hydrocarbon samples, including gasoline samples, using the method and the apparatus of the present invention.

The data of Table II demonstrates that the method is appropriate for sub-grade, regular, mid-grade and premium gasolines and also, hydrocarbon mixtures containing gasoline and ethanol (ETOH) or gasoline and methyl tertiary butyl ether (MTBE) or gasoline and tertiary amyl methyl ether (TAME). Additionally, the data indicate that the method and the apparatus can provide quantitative detection of fluorescent dyes in hydrocarbons at concentrations ranging from 25 to 100 parts per billion.

For the purposes of the present invention, "predominantly" is defined as more often than not. In quantitative terms, predominantly denotes about fifty per cent or more. "Substantially" is defined as being present in such proportions or occurring with sufficient frequency so as to measurably affect macroscopic qualities of an associated compound or system. Where the proportion or frequency required for measurable impact is not clear, substantially is to be regarded as twenty per cent or more. "Essentially" is defined as absolutely except that small variations which have no more than a negligible effect on macroscopic qualities and final outcome. Variations of about one per cent can often exist without causing a detectable change in essential qualities.

Examples have been presented and hypotheses advanced herein in order to better communicate certain facets of the invention. The scope of the invention is determined solely by the scope of the appended claims, and is not limited in any way by the Examples or the hypotheses. Moreover, practitioners who study the teachings set forth will undoubtedly receive suggestions which bring to mind many additional aspects of the invention. Such obviously similar aspects, whether or not expressly described herein, are intended to be within the scope of the present claims.

We claim as our invention:

1. A method for identifying a sample containing a tagged gasoline, which comprises:

irradiating a sample in an excitation band consisting of wavelengths of about 600 to about 2500 nanometers, said sample containing a tagged gasoline which includes an essentially metal-free fluorescent dye at a concentration of about 0.01 to about 1000 parts per billion by weight having a base state and an excited state, wherein the dye is selected from the group consisting of naphthalocyanine dye, phthalocyanine dye, cyanine dye, methine dye, croconium dye and squarylium dye, wherein the dye is soluble in gasoline to at least about one percent by weight based on the weight of the gasoline, wherein the dye is inert to water, and wherein the dye is capable of absorbing radiation in an absorption band consisting of wavelengths of about 600 to about 2500 nanometers associated with a transformation to the excited state and emitting radiation in a fluorescent band consisting of wavelengths of about 600 to about 2500 nanometers associated with a return to the base state, the excitation band overlapping the absorption band at an appropriate intensity to transform a significant portion of the dye from the base state to the excited state;

detecting the presence of radiation in the fluorescent band emanating from the sample;

generating a detection signal upon detecting at least a predetermined amount of emanated radiation in the fluorescent band; and identifying said tagged gasoline sample from the generated detection signal.

2. A method for identifying a gasoline sample containing a fluorescent dye, which comprises:

generating radiation in an excitation band consisting of wavelengths of about 600 to about 2500 nanometers, the radiation in the excitation band describing an excitation path extending from an excitation source to a target chamber;

irradiating by the excitation radiation without prior extraction or chromatographic separation a gasoline sample containing an essentially metal-free fluorescent dye at a concentration of about 0.01 to about 1000 parts per billion by weight, wherein the dye is soluble in gasoline to at least about one percent by weight based on the weight of the gasoline and said dye is selected from the group consisting of napththalocyanine dye, phthalocyanine dye, cyanine dye, methine dye, croconium dye, and squarylium dye, wherein the dye emits radiation in a fluorescent band consisting of wavelengths of about 600 to about 2500 nanometers as a result of exposure to radiation in the excitation band, and wherein the dye is inert to water;

passing radiation in the fluorescent band along a fluorescence path extending from the target chamber to a detector;

detecting the presence of a predetermined amount of fluorescence radiation at the detector and producing a detection signal; and identifying said gasoline sample from the detection signal.

3. The method of claim 2 wherein the excitation band includes wavelengths of about 630 to about 830 nanometers.

4. The method of claim 2 wherein the fluorescent band includes wavelengths of about 650 to about 850 nanometers.

5. The method of claim 2 wherein a final portion of the excitation path extending to the target chamber forms about a right angle to an initial portion of the fluorescence path emanating from the target chamber.

6. The method of claim 2 wherein the excitation source is a diode laser.

7. The method of claim 2 wherein the presence of the fluorescence radiation is determined by means of a silicon photodiode capable of producing an electrical signal as the detection signal.

8. The method of claim 2 which further comprises shielding the detector from radiation in the excitation band by means of a wavelength selective filter situated in the fluorescence path.

9. A method for tagging a gasoline, which comprises:

blending a fluorescent dye at a concentration of about 0.01 to about 1000 parts per billion by weight with a gasoline, wherein the dye is hydrocarbon-soluble to at least about one percent by weight in gasoline, wherein the dye is inert to water, wherein the dye comprises an essentially metal-free fluorescent dye selected from the group consisting of naphthalocyanine dye, phthalocyanine dye, cyanine dye, methine dye, croconium dye and squarylium dye, wherein the dye has a base state and an excited state, and wherein the dye is capable of absorbing radiation in an absorption band consisting of wavelengths of about 600 to about 2500 nanometers associated with a transformation to the excited state and, thereafter, emitting radiation in a fluorescent band consisting of wavelengths of about 600 to about 2500 nanometers associated with a return to the base state.

10. The method of claim 1, wherein the dye is selected from the group consisting of croconium dyes and squarylium dyes.

* * * * *